United States Patent [19]

Hartmann et al.

[11] 4,148,910
[45] Apr. 10, 1979

[54] N-METHYL-N-(SULPHONIC ACID AMIDE-N'-SULPHENYL)-CARBAMIC ACID ESTERS

[75] Inventors: Alfons Hartmann, Beckingen; Engelbert Kühle, Bergisch-Gladbach; Ingeborg Hammann, Cologne; Wolfgang Behrenz, Overath; Bernhard Homeyer, Leverkusen, all of Fed. Rep. of Germany

[73] Assignee: Bayer Aktiengesellschaft, Leverkusen, Fed. Rep. of Germany

[21] Appl. No.: 756,049

[22] Filed: Dec. 30, 1976

[30] Foreign Application Priority Data

Jan. 13, 1976 [DE] Fed. Rep. of Germany ....... 2600981

[51] Int. Cl.$^2$ ..................... A61N 9/16; C07D 307/86
[52] U.S. Cl. ..................... 424/285; 424/278; 424/282; 424/283; 424/300; 424/321; 260/327 M; 260/340.3; 260/340.7; 260/346.73; 260/465 D; 260/556 AR; 260/556 B; 260/556 N; 560/13; 560/115; 560/134; 560/135; 560/136; 560/137; 260/340.5 R; 260/340.9 R
[58] Field of Search ............. 260/346.73, 340.3, 340.5, 260/340.7, 340.9, 465 D; 560/13, 115, 134, 135, 136, 137; 424/278, 285, 282, 283, 300

[56] References Cited

U.S. PATENT DOCUMENTS 3,954,836   5/1976   Siegle et al. ..................... 260/470
3,980,673   9/1976   Siegle et al. ..................... 260/346.2 R

FOREIGN PATENT DOCUMENTS 2254359   5/1974   Fed. Rep. of Germany.
2434184   2/1976   Fed. Rep. of Germany.

*Primary Examiner*—Natalie Trousof
*Assistant Examiner*—Bernard Dentz
*Attorney, Agent, or Firm*—Sprung, Felfe, Horn, Lynch & Kramer

[57] ABSTRACT

N-Methyl-N-(sulphonic acid amide-N'-sulphenyl)-carbamic acid esters of the formula $$R^1-SO_2-N(R^2)-S-N(CH_3)-CO-O-R^3 \quad (I)$$

in which
R$^1$ is dialkylamino with 1 to 4 carbon atoms in each alkyl radical, phenyl or phenyl carrying at least one halogen, alkyl with 1 to 4 carbon atoms, nitro or trihalogenomethyl substituent,
R$^2$ is alkyl with 2 to 8 carbon atoms, cycloalkyl, phenyl or cycloalkyl or phenyl carrying at least one halogen, alkyl with 1 to 4 carbon atoms, nitro or trifluoromethyl substituent, and
R$^3$ is phenyl, naphthyl, benzodioxolanyl, dihydrobenzofuranyl or indanyl; phenyl, naphthyl, benzodioxolanyl, dihydrobenzofuranyl or indanyl substituted at least once by trihalogenomethyl, halogen, nitro, cyano, cycloalkyl, formamidino, dioxanyl or dioxolanyl, or by alkyl, alkenyl, alkynyl, alkoxy, alkenoxy, alkynoxy, alkylmercapto, alkenylmercapto, alkynylmercapto or dialkylamino, each with up to 4 carbon atoms per aliphatic moiety, or an oxime radical of the formula $$-N=C\begin{matrix}R^4\\R^5\end{matrix}$$

R$^4$ and R$^5$ each independently is cyano or alkyl, alkoxy, alkylthio, alkoxycarbonyl, dialkylcarbamoyl or dialkoxyphosphoryl with up to 4 carbon atoms per alkyl moiety, or
R$^4$ and R$^5$, conjointly with the adjacent carbon atom, form an optionally methyl- or phenyl-substituted dithiolane, dithiane, oxathiolane or oxathiane ring.

10 Claims, No Drawings

N-METHYL-N-(SULPHONIC ACID AMIDE-N'-SULPHENYL)-CARBAMIC ACID ESTERS

The present invention relates to and has for its objects the provision of particular new N-methyl-N-(sulphonic acid amide-N'-sulphenyl)-carbamic acid esters which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It has been disclosed in U.S. Pat. No. 3,954,836 and German Published Specification DOS No. 2,344,175 that N-sulphenylated carbamates, such as N-methyl-N-(p-chlorobenzenesulphonic acid methylamide-N'-sulphenyl)-carbamic acid α-naphthyl ester (Compound A), N-methyl-N-(benzenesulphonic acid methylamide-N'-sulphenyl)carbamic acid (thioacetic acid S-methyl ester)-oxime ester (Compound B), N-methyl-N-(p-toluenesulphonic acid methylamide-N'-sulphenyl)-carbamic acid (thioacetic acid S-methyl ester)-oxime ester (Compound C), N-methyl-N-(p-chlorobenzenesulphonic acid methylamide-N'-sulphenyl)-carbamic acid (thioacetic acid S-methyl ester)-oxime ester (Compound D) and N-methyl-N-(benzenesulphonic acid methylamide-N'-sulphenyl)-carbamic acid 3-isopropylphenyl ester (Compound E), possess insecticidal, acaricidal and fungicidal properties. However, their action is not always fully satisfactory, especially if low amounts are used.

The present invention now provides, as new compounds, the N-sulphenylated carbamates of the general formula

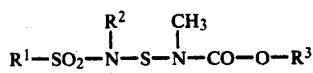
 (I)

in which
R$^1$ is dialkylamino with 1 to 4 carbon atoms in each alkyl radical, phenyl or phenyl carrying at least one halogen, alkyl with 1 to 4 carbon atoms, nitro or trihalogenomethyl substituent,
R$^2$ is alkyl with 2 to 8 carbon atoms, cycloalkyl, phenyl or cycloalkyl or phenyl carrying at least one halogen, alkyl with 1 to 4 carbon atoms, nitro or trifluoromethyl substituent, and
R$^3$ is phenyl, naphthyl, benzodioxolanyl, dihydrobenzofuranyl or indanyl; phenyl, naphthyl, benzodioxolanyl, dihydrobenzofuranyl or indanyl substituted at least once by trihalogenomethyl, halogen, nitro, cyano, cycloalkyl, formamidino, dioxanyl or dioxolanyl, or by alkyl, alkenyl, alkynyl, alkoxy, alkenoxy, alkynoxy, alkylmercapto, alkenylmercapto, alkynylmercapto or dialkylamino, each with up to 4 carbon atoms per aliphatic moiety, or an oxime radical of the formula

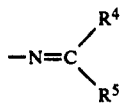

R$^4$ and R$^5$ each independently is cyano or alkyl, alkoxy, alkylthio, alkoxycarbonyl, dialkylcarbamoyl or dialkoxyphosphoryl with up to 4 carbon atoms per alkyl moiety, or
R$^4$ and R$^5$, conjointly with the adjacent carbon atom, form an optionally methyl- or phenyl-substituted dithiolane, dithiane, oxathiolane or oxathiane ring.

Preferably, R$^1$ represents dimethylamino or phenyl which can optionally be substituted by chlorine, methyl or trifluoromethyl, R$^2$ represents alkyl with 2 to 6 carbon atoms, cyclohexyl or phenyl, and R$^3$ represents phenyl which can optionally be substituted by alkyl with 1 to 3 carbon atoms, alkoxy with 1 to 3 carbon atoms, methylmercapto, dioxolanyl or methyl-substituted dioxolanyl, or represents benzodioxolanyl or dihydrobenzofuranyl which can optionally be substituted by methyl, or represents naphthyl or the oxime radical

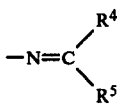

wherein R$^4$ and R$^5$ each represent alkyl with 1 to 4 carbon atoms, methylmercapto, cyano, dimethylaminocarbonyl or ethoxycarbonyl or represent, conjointly with the adjoining carbon atom, a dithiolane ring.

It is decidedly surprising that the compounds according to the invention exhibit a greater insecticidal, acaricidal and nematicidal action than the N-sulphenylated carbamates known from the state of the art. The materials according to the invention thus represent an enrichment of the art.

The present invention also provides a process for the preparation of an N-sulphenylated carbamate of the formula (I), which is obtained when a carbamic acid fluoride of the general formula

 (III), in which R$^1$ and R$^2$ have the abovementioned meanings, is reacted with a compound of the general formula

 (IV), in which R$^3$ has the abovementioned meaning,
if appropriate in the presence of an acid-binding agent and/or of a diluent.

If N-methyl-N-(benzenesulphonic acid propylamide-N'-sulphenyl)-carbamic acid fluoride and 1-methylthioacetaldoxime are used as starting materials, the course of the reaction can be represented by the following equation:

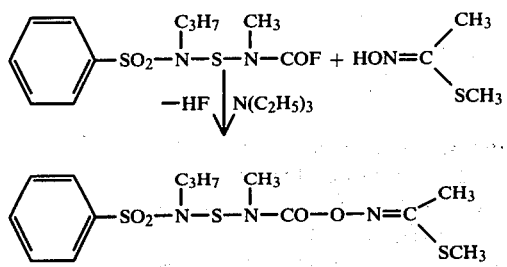

The phenols and oximes of the general formula (IV), used as starting materials, are known.

The carbamic acid fluorides of the formula (III), which are also employed, were not previously known, but can be prepared analogously to the process described in German Published Specification DOS No. 2,254,359. In this process, sulphonic acid chlorides are first reacted with primary amines to give the corresponding sulphonic acid amides. These are then converted, by means of disulphur dichloride, into disulphides. The scission of these disulphides with chlorine gives the corresponding sulphenechlorides, which can be reacted with N-methylcarbamic acid fluorides to give the carbamic acid fluorides of the formula (III).

It is preferred to use carbamic acid fluorides of the formula (III) in which $R^1$ represents dimethylamino, phenyl, 2-chlorophenyl, 3-chlorophenyl, 4-chlorophenyl, 3-trifluoromethylphenyl, 2-tolyl, 3-tolyl or 4-tolyl and $R^2$ represents ethyl, propyl, butyl, hexyl, cyclohexyl or phenyl.

If phenols of the formula (IV) are used as starting compounds, then $R^3$ preferably represents a phenyl, 2-isopropylphenyl, 3-isopropylphenyl, 2-isopropoxyphenyl, 3,5-dimethyl-4-methylmercaptophenyl, 3-methyl-4-dimethylaminophenyl, 4-nitrophenyl, 2-allyloxyphenyl, 3-sec.-butyl-4-methylphenyl, 4-methyl-3-isopropylphenyl, 2-dimethylaminophenyl, 2-(1',3'-dioxolanyl-(2'))-phenyl, 2-(4',5'-dimethyl-1',3'-dioxolanyl-(2'))-phenyl, 1-naphthyl, 4-(1,1-dimethylindanyl), 2,2-dimethylbenzodioxolanyl or 2,2-dimethyl-2,3-dihydrobenzofuranyl-(7) radical.

If oximes of the formula (IV) are used as starting compounds, then oximino-malonic acid diethyl ester, 2-oximino-1,3-dithiolane, 4-methyl-2-oximino-1,3-dithiolane, 4,4-dimethyl-2-oximino-1,3-dithiolane, 4-phenyl-2-oximino-1,3-dithioilane, 2-oximino-1,3-oxathilane, 2-oximino-1,3-dithiane, 2-oximino-1,3-oxathiane, hydroxyamylthioacetic acid S-methyl ester, α-methylmercapto-α-oximino-acetic acid ethyl ester, α-methylmercapto-α-oximino-N,N-dimethylacetamide or β,β-dimethyl-α-oximino-butyronitrile is preferably employed.

Suitable diluents are all inert organic solvents. These include ethers, such as diethyl ether, dioxane or tetrahydrofuran; hydrocarbons such as benzene or toluene; chlorohydrocarbons, such as methylene chloride, chloroform or chlorobenzene; nitriles and esters; and mixtures of these solvents.

To bind the hydrogen fluoride formed during the reaction, a tertiary organic base such as, for example, triethylamine or dimethylbenzylamine, is preferably added to the reaction mixture.

The reaction temperatures can be varied within a fairly wide range. In general, the reaction is carried out at between 0° and 100° C., preferably at from 20° to 60° C.

The reactants are usually employed in equimolar amounts, but the use of one component in excess is also possible, though it is not accompanied by any significant advantages.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillium vulgare* and *Porcellio scaber;* from the class of the Diplopoda, for example *Blaniulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order of the Mallophaga, for example Trichodectes spp. and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp.; Euxoa spp., Feltia spp., *Earias insulana,* Heliothis spp., *laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera,, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes crysocephala, Epilachna varivestis,* Atomaria spp., *Oryzaephilus surinamensis,* Anthonomus spp., Sitophilus spp., *Otiorrhynchus*

*sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus holoeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.; from the order of the Diptera, for example Aëdes spp., Anopheles spp., Culex spp., *Drosophila melanogaster,* Musca spp., Fannia spp., *Calliphora erythrocephala,* Lucilia spp., Crysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitta, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussion Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. averae particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hextare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods such as insects and acarids, and nematodes, which comprises applying to at least one correspondingly (a) such insects, (b) such acarids, (c) such nematodes and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Phaedon larvae test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all the beetle larvae had been killed, whereas 0% means that none of the beetle larvae had been killed.

The active compounds, the concentrations of the active compounds, the evaluation times and the results can be seen from the following table:

TABLE 1

(Insects which damage plants)
Phaedon larvae test

| Active compounds | Active compound concentration in % | Degree of destruction in % after 3 days |
|---|---|---|
| Cl—⟨C₆H₄⟩—SO₂—N(CH₃)—S—N(CH₃)—COO—naphthyl  (known) (A) | 0.1<br>0.01 | 100<br>0 |
| ⟨C₆H₅⟩—SO₂—N(CH₃)—S—N(CH₃)—COO—N=⟨thiazole⟩  (known) | 0.1<br>0.01 | 100<br>0 |
| Cl—⟨C₆H₄⟩—SO₂—N(C₄H₉)—S—N(CH₃)—CO—O—N=C(SCH₃)(COOC₂H₅)  (31) | 0.1<br>0.01 | 100<br>100 |
| Cl—⟨C₆H₄⟩—SO₂—N(C₄H₉)—S—N(CH₃)—CO—O—N=C(CN)(C(CH₃)₃)  (30) | 0.1<br>0.01 | 100<br>100 |
| ⟨C₆H₅⟩—SO₂—N(C₃H₇)—S—N(CH₃)—CO—O—⟨C₆H₃(CH₃)⟩—N(CH₃)₂  (26) | 0.1<br>0.01 | 100<br>100 |

TABLE 1—continued (Insects which damage plants)
Phaedon larvae test

| Active compounds | Active compound concentration in % | Degree of destruction in % after 3 days |
|---|---|---|
| (25) Ph-SO₂-N(C₃H₇)-S-N(CH₃)-CO-O-(2,6-diCH₃-4-SCH₃-phenyl) | 0.1<br>0.01 | 100<br>100 |
| (24) Ph-SO₂-N(C₃H₇)-S-N(CH₃)-CO-O-(2-OC₃H₇i-phenyl) | 0.1<br>0.01 | 100<br>100 |
| (28) Ph-SO₂-N(C₃H₇)-S-N(CH₃)-CO-O-naphthyl | 0.1<br>0.01 | 100<br>85 |
| (27) Ph-SO₂-N(C₃H₇)-S-N(CH₃)-CO-O-(2-(1,3-dioxolan-2-yl)-phenyl) | 0.1<br>0.01 | 100<br>100 |
| (8) Ph-SO₂-N(C₃H₇)-S-N(CH₃)-CO-O-(2,2-dimethylbenzodihydropyran) | 0.1<br>0.01 | 100<br>100 |
| (22) 2-CH₃-C₆H₄-SO₂-N(C₄H₉)-S-N(CH₃)-CO-O-(2,2-dimethylbenzodihydropyran) | 0.1<br>0.01 | 100<br>100 |
| (15) 4-CH₃-C₆H₄-SO₂-N(C₂H₅)-S-N(CH₃)-CO-O-(2,2-dimethylbenzodihydropyran) | 0.1<br>0.01 | 100<br>100 |
| (2) 4-CH₃-C₆H₄-SO₂-N(C₃H₇)-S-N(CH₃)-CO-O-(2,2-dimethylbenzodihydropyran) | 0.1<br>0.01 | 100<br>100 |
| (11) 4-CH₃-C₆H₄-SO₂-N(C₄H₉)-S-N(CH₃)-CO-O-(2,2-dimethylbenzodihydropyran) | 0.1<br>0.01 | 100<br>100 |

TABLE 1—continued
(Insects which damage plants)
Phaedon larvae test
| Active compounds | Active compound concentration in % | Degree of destruction in % after 3 days |
|---|---|---|
| 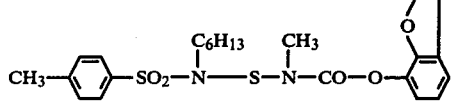 (13) | 0.1<br>0.01 | 100<br>100 |
|  (14) | 0.1<br>0.01 | 100<br>95 |
|  (9) | 0.1<br>0.01 | 100<br>100 |
| 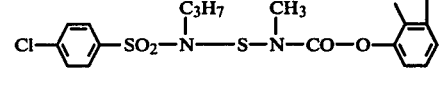 (12) | 0.1<br>0.01 | 100<br>100 |
| 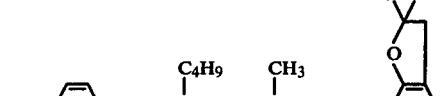 (21) | 0.1<br>0.01 | 100<br>100 |
|  (39) | 0.1<br>0.01 | 100<br>100 |
| 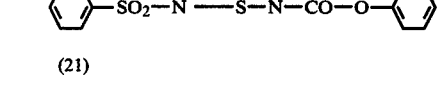 (40) | 0.1<br>0.01 | 100<br>100 |
| 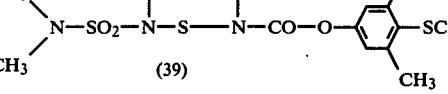 (38) | 0.1<br>0.01 | 100<br>100 |

TABLE 1—continued (Insects which damage plants)
Phaedon larvae test

| Active compounds | Active compound concentration in % | Degree of destruction in % after 3 days |
|---|---|---|
| Compound (42): (CH$_3$)$_2$N—SO$_2$—N(C$_6$H$_5$)—S—N(CH$_3$)—CO—O—[2-(4-methyl-1,3-dioxolan-2-yl)phenyl] | 0.1<br>0.01 | 100<br>100 |
| Compound (36): (CH$_3$)$_2$N—SO$_2$—N(C$_3$H$_7$)—S—N(CH$_3$)—CO—O—[2-(4,4-dimethyl-1,3-dioxan-2-yl)phenyl] | 0.1<br>0.01 | 100<br>100 |
| Compound (37): (CH$_3$)$_2$N—SO$_2$—N(C$_4$H$_9$)—S—N(CH$_3$)—CO—O—[2-(4,4-dimethyl-1,3-dioxan-2-yl)phenyl] | 0.1<br>0.01 | 100<br>100 |
| Compound (33): C$_6$H$_5$—SO$_2$—N(C$_3$H$_7$)—S—N(CH$_3$)—CO—O—[2-(2,2-dimethyl-1,3-dioxolan-2-yl)phenyl] | 0.1<br>0.01 | 100<br>100 |

EXAMPLE 2

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following table:

TABLE 2

(Insects which damage plants)
Myzus test

| Active compounds | Active compound concentration in % | Degree of destruction |
|---|---|---|
| (known) (E): C$_6$H$_5$—SO$_2$—N(CH$_3$)—S—N(CH$_3$)—COO—(iC$_3$H$_7$-phenyl) | 0.1<br>0.01 | 90<br>0 |
| (known) (A): Cl—C$_6$H$_4$—SO$_2$—N(CH$_3$)—S—N(CH$_3$)—COO—naphthyl | 0.1<br>0.01 | 90<br>0 |

TABLE 2—continued (Insects which damage plants)
Myzus test

| Active compounds | Active compound concentration in % | Degree of destruction |
|---|---|---|
| (20) H₃C–C₆H₄–SO₂–N(C₄H₉)–S–N(CH₃)–CO–O–N=C(CH₃)(SCH₃) | 0.1<br>0.01 | 100<br>100 |
| (16) CH₃–C₆H₄–SO₂–N(C₆H₁₃)–S–N(CH₃)–CO–O–N=C(CH₃)(SCH₃) | 0.1<br>0.01 | 99<br>85 |
| (18) CH₃–C₆H₄–SO₂–N(C₆H₁₁)–S–N(CH₃)–CO–O–N=C(CH₃)(SCH₃) | 0.1<br>0.01 | 100<br>99 |
| (29) Cl–C₆H₄–SO₂–N(C₄H₉)–S–N(CH₃)–CO–O–N=C(dithiolane) | 0.1<br>0.01 | 100<br>100 |
| (23) C₆H₅–SO₂–N(C₃H₇)–S–N(CH₃)–CO–O–C₆H₄(iC₃H₇) | 0.1<br>0.01 | 100<br>98 |
| 34  (CH₃)₂N–SO₂–N(C₃H₇)–CO–O–N=C(CH₃)(SCH₃) | 0.1<br>0.01 | 100<br>99 |
| 35  (CH₃)₂N–SO₂–N(C₄H₉)–S–N(CH₃)–CO–O–N=C(CH₃)(SCH₃) | 0.1<br>0.01 | 100<br>100 |

EXAMPLE 3

Doralis test (systemic action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier, and the concentrate was diluted with water to the desired concentration.

Bean plants (*Vicia faba*) which had been heavily infested with the bean aphid (*Doralis fabae*) were each watered with 20 ml of the preparation of the active compound so that this preparation penetrated into the soil without wetting the leaves of the bean plants. The active compound was taken up from the soil by the bean plants and thus passed to the infested leaves.

After the specified periods of time, the degree of destruction was determined as a percentage. 100% means that all the aphids were killed; 0% means that none of the aphids were killed.

The active compounds, the concentrations of the active compounds, the evaluation times and the results can be seen from the following table:

TABLE 3

(Insects which damage plants)
Doralis test
(systemic action)

| Active compounds | Active compound concentration in % | Degree of destruction in % after 4 days |
|---|---|---|
| C₆H₅–SO₂–N(CH₃)–S–N(CH₃)–COO–C₆H₄(C₃H₇i)  (known) (E) | 0.1<br>0.01 | 100<br>0 |

TABLE 3—continued (Insects which damage plants)
Doralis test
(systemic action)

| Active compounds | Active compound concentration in % | Degree of destruction in % after 4 days |
|---|---|---|
| CH₃–C₆H₄–SO₂–N(CH₃)–S–N(CH₃)–COO–N=C(CH₃)(SCH₃)  (known) (C) | 0.1<br>0.01 | 100<br>0 |
| CH₃–C₆H₄–SO₂–N(C₂H₅)–S–N(CH₃)–CO–O–N=C(CH₃)(SCH₃)  (17) | 0.1<br>0.01 | 100<br>99 |
| C₆H₅–SO₂–N(C₃H₇)–S–N(CH₃)–CO–O–N=C(CH₃)(SCH₃)  (3) | 0.1<br>0.01 | 100<br>100 |
| CH₃–C₆H₄–SO₂–N(C₃H₇)–S–N(CH₃)–CO–O–N=C(CH₃)(SCH₃)  (1) | 0.1<br>0.01 | 100<br>100 |
| Cl–C₆H₄–SO₂–N(C₃H₇)–S–N(CH₃)–CO–O–N=C(CH₃)(SCH₃)  (4) | 0.1<br>0.01 | 100<br>100 |
| C₆H₅–SO₂–N(C₄H₉)–S–N(CH₃)–CO–O–N=C(CH₃)(SCH₃)  (5) | 0.1<br>0.01 | 100<br>100 |
| o-CH₃–C₆H₄–SO₂–N(C₄H₉)–S–N(CH₃)–CO–O–N=C(CH₃)(SCH₃)  (19) | 0.1<br>0.01 | 100<br>100 |
| CH₃–C₆H₄–SO₂–N(C₄H₉)–S–N(CH₃)–CO–O–N=C(CH₃)(SCH₃)  (6) | 0.1<br>0.01 | 100<br>100 |
| Cl–C₆H₄–SO₂–N(C₄H₉)–S–N(CH₃)–CO–O–N=C(CH₃)(SCH₃)  (7) | 0.1<br>0.01 | 100<br>100 |
| (CH₃)₂N–SO₂–N(C₆H₅)–N–S–N(CH₃)–CO–O–C₆H₄(OC₃H₇i)  (43) | 0.1<br>0.01 | 100<br>100 |

EXAMPLE 4

Tetranychus test (resistant)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with wateer to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed, whereas 0% means that none of the spider mites were killed.

The active compounds, the concentrations of the active compounds, the evaluation times and the results can be seen from the following table:

TABLE 4

(Mites which damage plants)
Tetranychus test

| Active compounds | Active compound concentration in % | Degree of destruction in % after 2 days |
|---|---|---|
| $CH_3-\text{C}_6H_4-SO_2-N(CH_3)-S-N(CH_3)-COO-N=C(CH_3)(SCH_3)$ (C) (known) | 0.1 | 0 |
| $Cl-C_6H_4-SO_2-N(C_4H_9)-S-N(CH_3)-CO-O-N=C(CN)-C(CH_3)_3$ (30) | 0.1 | 100 |

EXAMPLE 5

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount by weight of active compound per unit volume of soil, which is given hereinafter in ppm (=mg/liter) was decisive. The treated soil was filled into pots and these were planted with cabbage (*Brassica oleracea*). The active compound could in this way be absorbed from the soil by the roots of the plants and be transported into the leaves.

In order to demonstrate the root-systemic effect, exclusively the leaves were infested with the abovementioned test insects after 7 days. After a further 2 days, the evaluation was carried out by counting or estimating the dead insects. The root-systemic action of the active compound was derived from the mortality figures. It was 100% if all the test insects had been killed and 0% if just as many test insects survived as in the case of the untreated control.

The active compounds, the amounts used and the results can be seen from the table which follows:

TABLE 5

Root-systemic action
*Myzus persicae*

| Active compound | Degree of destruction in % at an active compound concentration of 10 ppm |
|---|---|
| $C_6H_5-SO_2-N(CH_3)-S-N(CH_3)-COO-C_6H_4-i\text{-}C_3H_7$ (known) (E) | 0% |
| $Cl-C_6H_4-SO_2-N(CH_3)-S-N(CH_3)-COO-N=C(CH_3)(SCH_3)$ (known) (D) | 0% |
| $Cl-C_6H_4-SO_2-N(CH_3)-S-N(CH_3)-COO-\text{naphthyl}$ (known) (A) | 0% |
| $(CH_3)_2N-SO_2-N(C_6H_5)-S-N(CH_3)-CO-O-C_6H_4-O-C(CH_3)_2$ (38) | 100% |

TABLE 5—continued

Root-systemic action
*Myzus persicae*

| Active compound | Degree of destruction in % at an active compound concentration of 10 ppm |
|---|---|
| (8) C₆H₅—SO₂—N(C₃H₇)—S—N(CH₃)—CO—O—[2,2-dimethyl-2,3-dihydrobenzofuran-7-yl] | 100% |
| (2) 4-CH₃-C₆H₄—SO₂—N(C₃H₇)—S—N(CH₃)—CO—O—[2,2-dimethyl-2,3-dihydrobenzofuran-7-yl] | 100% |
| (9) 4-Cl-C₆H₄—SO₂—N(C₃H₇)—S—N(CH₃)—CO—O—[2,2-dimethyl-2,3-dihydrobenzofuran-7-yl] | 100% |
| (10) C₆H₅—SO₂—N(C₄H₉)—S—N(CH₃)—CO—O—[2,2-dimethyl-2,3-dihydrobenzofuran-7-yl] | 100% |
| (11) 4-CH₃-C₆H₄—SO₂—N(C₄H₉)—S—N(CH₃)—CO—O—[2,2-dimethyl-2,3-dihydrobenzofuran-7-yl] | 100% |
| (12) 4-Cl-C₆H₄—SO₂—N(C₄H₉)—S—N(CH₃)—CO—O—[2,2-dimethyl-2,3-dihydrobenzofuran-7-yl] | 100% |
| (15) 4-CH₃-C₆H₄—SO₂—N(C₂H₅)—S—N(CH₃)—CO—O—[2,2-dimethyl-2,3-dihydrobenzofuran-7-yl] | 100% |
| (31) 4-Cl-C₆H₄—SO₂—N(C₄H₉)—S—N(CH₃)—CO—O—N=C(SCH₃)(COOC₂H₅) | 100% |

TABLE 5—continued

Root-systemic action
*Myzus persicae*

| Active compound | Degree of destruction in % at an active compound concentration of 10 ppm |
|---|---|
| (21) F$_3$C—C$_6$H$_4$—SO$_2$—N(C$_4$H$_9$)—S—N(CH$_3$)—CO—O—[2,2-dimethyl-benzodioxole] | 100% |

EXAMPLE 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/liter), was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

TABLE 6

*Meloidogyne incognita*

| Active compound | Degree of destruction in % at an active compound concentration 10 ppm |
|---|---|
| C$_6$H$_5$—SO$_2$—N(CH$_3$)—S—N(CH$_3$)—COO—C$_6$H$_4$-i-C$_3$H$_7$ (known) (E) | 0% |
| Cl—C$_6$H$_4$—SO$_2$—N(CH$_3$)—S—N(CH$_3$)—COO—naphthyl (known) (A) | 0% |
| C$_6$H$_5$—SO$_2$—N(C$_3$H$_7$)—S—N(CH$_3$)—CO—O—N=C(CH$_3$)(SCH$_3$) (3) | 100% |
| CH$_3$—C$_6$H$_4$—SO$_2$—N(C$_3$H$_7$)—S—N(CH$_3$)—CO—O—N=C(CH$_3$)(SCH$_3$) (1) | 100% |
| Cl—C$_6$H$_4$—SO$_2$—N(C$_3$H$_7$)—S—N(CH$_3$)—CO—O—N=C(CH$_3$)(SCH$_3$) (4) | 100% |
| CH$_3$—C$_6$H$_4$—SO$_2$—N(C$_4$H$_9$)—S—N(CH$_3$)—CO—O—N=C(CH$_3$)(SCH$_3$) (6) | 100% |

TABLE 6-continued
_Meloidogyne incognita_
| Active compound | Degree of destruction in % at an active compound concentration 10 ppm |
|---|---|
| 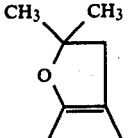 (8) | 100% |
| 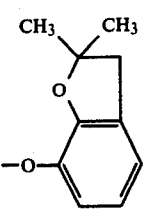 (15) | 100% |
| 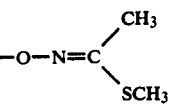 (17) | 100% |
| 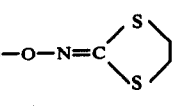 (29) | 100% |
| 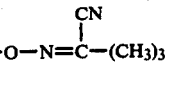 (30) | 100% |
| 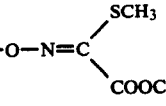 (31) | 100% |
| 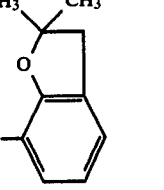 (22) | 100% |
| 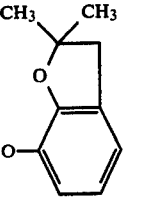 (21) | 100% |
| 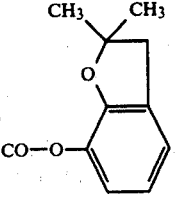 (2) | 100% |

TABLE 6-continued
*Meloidogyne incognita*
| Active compound | Degree of destruction in % at an active compound concentration 10 ppm |
|---|---|
| 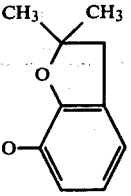 (9) | 100% |
|  (10) | 100% |
| 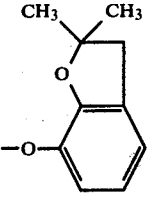 (11) | 100% |
| 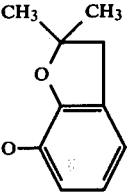 (12) | 100% |
| 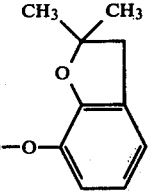 (13) | 100% |
| 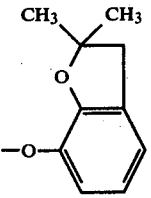 (14) | 100% |
| 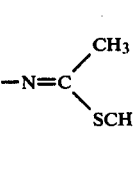 (19) | 100% |
| 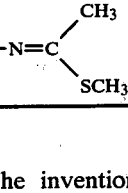 (20) | 100% |
The compounds according to the invention also showed a particularly good activity in a test using the insects *Phorbia antiqua*.
EXAMPLE 7
Mosquito larvae test
Test insects: *Aëdes aegypti*

Solvent: 99 parts by weight of acetone
Emulsifier: 1 part by weight of benzylhydroxydiphenyl polyglycol ether To produce a suitable preparation of active compound, 2 parts by weight of the active compound were dissolved in 1,000 parts by volume of the solvent containing the amount of emulsifier stated above. The solution thus obtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage. 100% means that all the larvae were killed. 0% means that no larvae at all were killed.

The active compounds, the concentrations of the active compounds, the test insects and the results can be seen from the following table:

TABLE 7

Mosquito larvae test

| Active compound | Active compound concentration of the solution in ppm | Degree of destruction in % |
|---|---|---|
| C₆H₅—SO₂—N(CH₃)—S—N(CH₃)—COO—N=C(CH₃)(SCH₃) (known) | 10 | 40 |
| Cl—C₆H₄—SO₂—N(CH₃)—S—N(CH₃)—COO—naphthyl (known) (A) | 10 | 80 |
| C₆H₅—SO₂—N(CH₃)—S—N(CH₃)—COO—N=C(S-CH₂-CH₂-S) (known) (F) | 10 | 90 |
| CH₃—C₆H₄—SO₂—N(C₂H₅)—S—N(CH₃)—CO—O—(2,2-dimethylbenzofuran-7-yl) (15) | 0.1 | 100 |
| C₆H₅—SO₂—N(C₃H₇)—S—N(CH₃)—CO—O—(3,5-dimethyl-4-methylthiophenyl) (25) | 1 | 95 |
| C₆H₅—SO₂—N(C₃H₇)—S—N(CH₃)—CO—O—(2,2-dimethylbenzofuran-7-yl) (8) | 0.1 | 100 |
| CH₃—C₆H₄—SO₂—N(C₃H₇)—S—N(CH₃)—CO—O—(2,2-dimethylbenzofuran-7-yl) (2) | 0.1 | 100 |

TABLE 7—continued

Mosquito larvae test

| Active compound | Active compound concentration of the solution in ppm | Degree of destruction in % |
|---|---|---|
| (9) 4-Cl-C6H4-SO2-N(C3H7)-S-N(CH3)-CO-O-(2,2-dimethyl-2,3-dihydrobenzofuran-7-yl) | 0.1 | 100 |
| (10) C6H5-SO2-N(C4H9)-S-N(CH3)-CO-O-(2,2-dimethyl-2,3-dihydrobenzofuran-7-yl) | 0.1 | 100 |
| (11) 4-CH3-C6H4-SO2-N(C4H9)-S-N(CH3)-CO-O-(2,2-dimethyl-2,3-dihydrobenzofuran-7-yl) | 0.1 | 100 |
| (12) 4-Cl-C6H4-SO2-N(C4H9)-S-N(CH3)-CO-O-(2,2-dimethyl-2,3-dihydrobenzofuran-7-yl) | 0.1 | 100 |
| (14) 4-CH3-C6H4-SO2-N(cyclohexyl)-S-N(CH3)-CO-O-(2,2-dimethyl-2,3-dihydrobenzofuran-7-yl) | 0.1 | 100 |
| (41) (CH3)2N-SO2-N(C6H5)-S-N(CH3)-CO-O-(2-isopropylphenyl) | 1 | 100 |
| (30) 4-Cl-C6H4-SO2-N(C4H9)-S-N(CH3)-CO-O-N=C(CN)-C(CH3)3 | 0.1 | 100 |
| (38) (CH3)2N-SO2-N(C6H5)-S-N(CH3)-CO-O-(2,2-dimethyl-2,3-dihydrobenzofuran-7-yl) | 1 | 100 |

EXAMPLE 8

LD$_{100}$ test
Test insects: *Sitophilus granarius*
Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. After 25 test insects were then placed in the Petri dish and it was covered with a glass lid.

The condition of the test insects was observed 3 days after the commencement of the experiments. The destruction, in %, was determined.

The active compounds, the concentrations of the active compounds, the test insects and the results can be seen from the following table:

TABLE 8

LD$_{100}$ test/*Sitophilus granarius*

| Active compounds | Active compound concentration % strength solution | Destruction in % |
|---|---|---|
| (known) (B) — C$_6$H$_5$—SO$_2$—N(CH$_3$)—S—N(CH$_3$)—COO—N=C(CH$_3$)(SCH$_3$) | 0.2 | 0 |
| (known) (A) — 4-Cl-C$_6$H$_4$—SO$_2$—N(CH$_3$)—S—N(CH$_3$)—COO—naphthyl | 0.2 | 0 |
| (known) (F) — C$_6$H$_5$—SO$_2$—N(CH$_3$)—S—N(CH$_3$)—COO—N=C(S—CH$_2$—CH$_2$—S) | 0.2 | 80 |
| (15) — 4-CH$_3$-C$_6$H$_4$—SO$_2$—N(C$_2$H$_5$)—S—N(CH$_3$)—CO—O—(2,2-dimethyl-2,3-dihydrobenzofuran-7-yl) | 0.02 | 100 |
| (8) — C$_6$H$_5$—SO$_2$—N(C$_3$H$_7$)—S—N(CH$_3$)—CO—O—(2,2-dimethyl-2,3-dihydrobenzofuran-7-yl) | 0.02 | 100 |
| (2) — 4-CH$_3$-C$_6$H$_4$—SO$_2$—N(C$_3$H$_7$)—S—N(CH$_3$)—CO—O—(2,2-dimethyl-2,3-dihydrobenzofuran-7-yl) | 0.02 | 100 |
| (9) — 4-Cl-C$_6$H$_4$—SO$_2$—N(C$_3$H$_7$)—S—N(CH$_3$)—CO—O—(2,2-dimethyl-2,3-dihydrobenzofuran-7-yl) | 0.02 | 100 |

TABLE 8—continued

LD$_{100}$ test/*Sitophilus granarius*

| Active compounds | Active compound concentration % strength solution | Destruction in % |
|---|---|---|
| 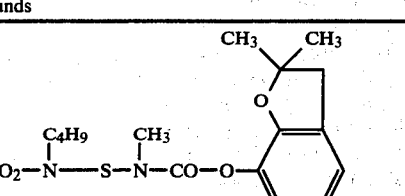 (10) | 0.02 | 100 |
| 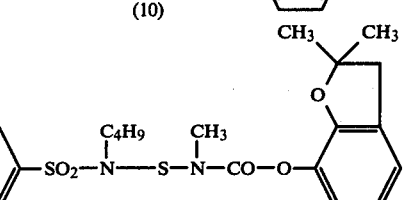 (11) | 0.2<br>0.02 | 100<br>80 |
| 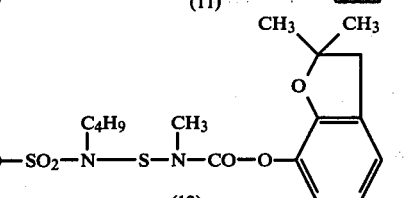 (12) | 0.02 | 100 |
| 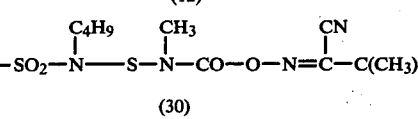 (30) | 0.2<br>0.02 | 100<br>90 |

The process of the present invention is illustrated by the following examples, wherein Examples 9 and 10 illustrate the method of preparation of the starting compounds of general formula III:

EXAMPLE 9

(a) 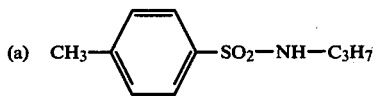

165 g. (2.8 moles) of n-propylamine were added dropwise to a solution of 250 g. (1.31 moles) of p-tosyl chloride in 2 liters of toluene. The mixture was heated under reflux for 4 hours and extracted by shaking with water, and the organic phase was dried over sodium sulphate and concentrated in vacuo. 264 g. of a colorless oil remained.

(b) 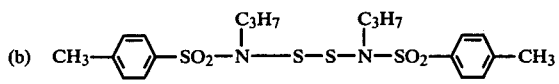

264 g. (1.24 moles) of the oil obtained as described above and 190 ml (1.36 moles) of triethylamine were dissolved in 2 liters of toluene. 83.7 g. (0.62 mole) of disulphur dichloride were added dropwise at room temperature. The mixture was stirred for 6 hours at room temperature and for a further hour at 40° C. and was extracted by shaking twice with water and once with 10% strength aqueous ammonium chloride solution; the organic phase was dried over sodium sulphate and concentrated in vacuo. The residue was recrystallized from methanol. Yield: 205 g. of disulphide of melting point 88°–89° C.

(c) 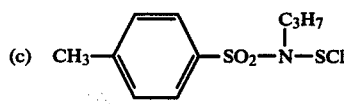

71 g. (1 mole) of chlorine gas were passed into a solution of of 205 g. (0.42 mole) of the disulphide prepared as described above, in 1 liter of chloroform, at room temperature. The mixture was then stirred for a further 8 hours and was left to stand overnight, after which it was concentrated in vacuo. 234 g. of sulphenechloride were obtained in the form of an orange-colored oil.

(d) 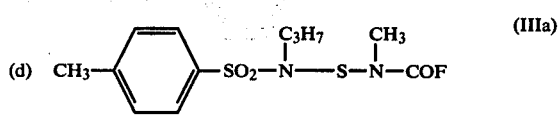 (IIIa)

125 ml (0.9 mole) of triethylamine were added dropwise, at room temperature, to a solution of 234 g. (0.84 mole) of the sulphene-chloride obtained as described above and 64.7 g. (0.84 mole) of N-methylcarbamic acid fluoride in 1 liter of toluene at room temperature. The mixture was stirred further for 6 hours at 25° C. and 1 hour at 40° C. and was extracted by shaking twice with water and twice with 10 per cent strength aqueous ammonium chloride solution; the organic phase was dried over sodium sulphate and concentrated in vacuo. 226 g. of acid fluoride were obtained in the form of a brown oil; $n_D^{20} = 1.5368$.

The following were prepared by an analogous method of synthesis:

TABLE 9

(IIIb) CH₃—⟨phenyl⟩—SO₂—N(C₄H₉)—S—N(CH₃)—COF (IIIc) ⟨phenyl⟩—SO₂—N(C₃H₇)—S—N(CH₃)—COF (IIId) ⟨phenyl⟩—SO₂—N(C₄H₉)—S—N(CH₃)—COF (IIIe) Cl—⟨phenyl⟩—SO₂—N(C₃H₇)—S—N(CH₃)—COF (IIIf) Cl—⟨phenyl⟩—SO₂—N(C₄H₉)—S—N(CH₃)—COF (IIIg) CH₃—⟨phenyl⟩—SO₂—N(C₂H₅)—S—N(CH₃)—COF (IIIh) CH₃—⟨phenyl⟩—SO₂—N(C₆H₁₃)—S—N(CH₃)—COF (IIIi) CH₃—⟨phenyl⟩—SO₂—N(cyclohexyl-H)—S—N(CH₃)—COF (IIIj) 2-CH₃-⟨phenyl⟩—SO₂—N(C₄H₉)—S—N(CH₃)—COF (IIIk) F₃C—⟨phenyl⟩—SO₂—N(C₄H₉)—S—N(CH₃)—COF (IIIl) (CH₃)₂N—SO₂—N(C₃H₇)—S—N(CH₃)—COF (IIIm) (CH₃)₂N—SO₂—N(C₄H₉)—S—N(CH₃)—COF

EXAMPLE 10

(a) 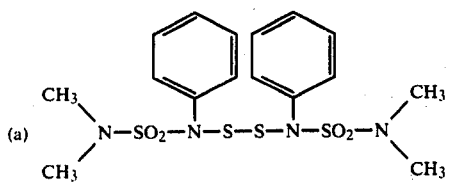

2.3 g. (0.1 mole) of sodium were dissolved in 150 ml of absolute methanol. 20 g. (0.1 mole) of dimethylamidosulphonic acid anilide were added and the mixture was stirred for 12 hours at 25° C. It was then concentrated and the residue was dried in a high vacuum at 80° C. The salt thus obtained was suspended in 30 ml of toluene. 6.75 g. (0.05 mole) of disulphur dichloride were added dropwise, the mixture was stirred for 12 hours at 25° C., the sodium chloride which had precipitated was filtered off and the filtrate was concentrated in vacuo on a rotary evaporator at a maximum bath temperature of 50° C. The residue was extracted by stirring with methanol, giving 8.6 g. of disulphide of melting point 116° C.

(b) 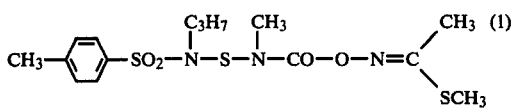

3.4 g. of sulphuryl chloride were added to a suspension of 11.5 g. (0.025 mole) of the disulphide, prepared as described above, in 10 ml of carbon tetrachloride, and the mixture was warmed for 2 hours under reflux and was then concentrated. The oil which remained crystallized after a short time.

(c) (CH₃)₂N—SO₂—N(⟨phenyl⟩)—S—N(CH₃)—COF 16 g. (0.16 mole) of triethylamine were added dropwise, at room temperature, to a solution of 37.2 g. (0.15 mole) of the sulphene-chloride, prepared as described above, and 11.6 g. (0.15 mole) of N-methylcarbamic acid fluoride in 500 ml of toluene. The mixture was stirred for 8 hours at 25° C. and ½ hour at 40° C. and was filtered; the filtrate was concentrated in vacuo. The crystalline residue was washed with ether.

Yield: 15 g.: melting point 84°–85° C.

EXAMPLE 11

CH₃—⟨phenyl⟩—SO₂—N(C₃H₇)—S—N(CH₃)—CO—O—N=C(CH₃)(SCH₃)   (1)

8 ml (0.055 mole) of triethylamine were added dropwise, at 25° C., to 16 g (0.05 mole) of N-methyl-N-(4-toluenesulphonic acid propylamide-N′-sulphenyl)-carbamic acid fluoride (Example 9d) and 5.25 g (0.05 mole) of hydroxamylthioacetic acid S-methyl ester in 250 ml of toluene. The reaction mixture was stirred for 1 hour at this temperature and for 2 hours at 50°–60° C. and was then shaken with water. The organic phase was separated off and washed twice with 10% strength aqueous ammonium chloride solution and then dried over sodium sulphate, and the solvent was distilled off in vacuo. An oily residue remained.

Yield: 16 g (82% of theory); $n_D^{20} = 1.5634$.

The following compounds were prepared analogously:

TABLE 10

| Compound No. | Formula | Physical properties |
|---|---|---|
| 2 | CH$_3$-C$_6$H$_4$-SO$_2$-N(C$_3$H$_7$)-S-N(CH$_3$)-CO-O-(2,2-dimethyl-2,3-dihydrobenzofuran-7-yl) | viscous oil |
| 3 | C$_6$H$_5$-SO$_2$-N(C$_3$H$_7$)-S-N(CH$_3$)-CO-O-N=C(CH$_3$)(SCH$_3$) | melting point 98° C. |
| 4 | 4-Cl-C$_6$H$_4$-SO$_2$-N(C$_3$H$_7$)-S-N(CH$_3$)-CO-O-N=C(CH$_3$)(SCH$_3$) | melting point 84° C. |
| 5 | C$_6$H$_5$-SO$_2$-N(C$_4$H$_9$)-S-N(CH$_3$)-CO-O-N=C(CH$_3$)(SCH$_3$) | melting point 101° C. |
| 6 | CH$_3$-C$_6$H$_4$-SO$_2$-N(C$_4$H$_9$)-S-N(CH$_3$)-CO-O-N=C(CH$_3$)(SCH$_3$) | melting point 30° C. $n_D^{20} = 1.5608$ |
| 7 | 4-Cl-C$_6$H$_4$-SO$_2$-N(C$_4$H$_9$)-S-N(CH$_3$)-CO-O-N=C(CH$_3$)(SCH$_3$) | $n_D^{20} = 1.5681$ |
| 8 | C$_6$H$_5$-SO$_2$-N(C$_3$H$_7$)-S-N(CH$_3$)-CO-O-(2,2-dimethyl-2,3-dihydrobenzofuran-7-yl) | $n_D^{20} = 1.5523$ |
| 9 | 4-Cl-C$_6$H$_4$-SO$_2$-N(C$_3$H$_7$)-S-N(CH$_3$)-CO-O-(2,2-dimethyl-2,3-dihydrobenzofuran-7-yl) | viscous oil |
| 10 | C$_6$H$_5$-SO$_2$-N(C$_4$H$_9$)-S-N(CH$_3$)-CO-O-(2,2-dimethyl-2,3-dihydrobenzofuran-7-yl) | $n_D^{20} = 1.5508$ |
| 11 | CH$_3$-C$_6$H$_4$-SO$_2$-N(C$_4$H$_9$)-S-N(CH$_3$)-CO-O-(2,2-dimethyl-2,3-dihydrobenzofuran-7-yl) | $n_D^{20} : 1.5515$ |

TABLE 10—continued

| Compound No. | Formula | Physical properties |
|---|---|---|
| 12 | 4-Cl-C6H4-SO2-N(C4H9)-S-N(CH3)-CO-O-(2,2-dimethyl-2,3-dihydrobenzofuran-7-yl) | $n_D^{20}$: 1.5520 |
| 13 | 4-CH3-C6H4-SO2-N(C6H13)-S-N(CH3)-CO-O-(2,2-dimethyl-2,3-dihydrobenzofuran-7-yl) | $n_D^{20}$: 1.5489 |
| 14 | 4-CH3-C6H4-SO2-N(cyclohexyl)-S-N(CH3)-CO-O-(2,2-dimethyl-2,3-dihydrobenzofuran-7-yl) | viscous oil |
| 15 | 4-CH3-C6H4-SO2-N(C2H5)-S-N(CH3)-CO-O-(2,2-dimethyl-2,3-dihydrobenzofuran-7-yl) | viscous oil |
| 16 | 4-CH3-C6H4-SO2-N(C6H13)-S-N(CH3)-CO-O-N=C(CH3)(SCH3) | $n_D^{20}$: 1.5430 |
| 17 | 4-CH3-C6H4-SO2-N(C2H5)-S-N(CH3)-CO-O-N=C(CH3)(SCH3) | viscous oil |
| 18 | 4-CH3-C6H4-SO2-N(cyclohexyl)-S-N(CH3)-CO-O-N=C(CH3)(SCH3) | viscous oil |
| 19 | 2-CH3-C6H4-SO2-N(C4H9)-S-N(CH3)-CO-O-N=C(CH3)(SCH3) | melting point 100° C. |
| 20 | 3-F3C-C6H4-SO2-N(C4H9)-S-N(CH3)-CO-O-N=C(CH3)(SCH3) | $n_D^{20}$: 1.5188 |
| 21 | 3-F3C-C6H4-SO2-N(C4H9)-S-N(CH3)-CO-O-(2,2-dimethyl-2,3-dihydrobenzofuran-7-yl) | $n_D^{20}$: 1.5185 |

TABLE 10—continued

| Compound No. | Formula | Physical properties |
|---|---|---|
| 22 | 2-CH₃-C₆H₄-SO₂-N(C₄H₉)-S-N(CH₃)-CO-O-(2,2-dimethyl-2,3-dihydrobenzofuran-7-yl) | $n_D^{20}$: 1.5448 |
| 23 | C₆H₅-SO₂-N(C₃H₇)-S-N(CH₃)-CO-O-(2-iC₃H₇-C₆H₄) | $n_D^{20}$: 1.5462 |
| 24 | C₆H₅-SO₂-N(C₃H₇)-S-N(CH₃)-CO-O-(2-OC₃H₇i-C₆H₄) | $n_D^{20}$: 1.5462 |
| 25 | C₆H₅-SO₂-N(C₃H₇)-S-N(CH₃)-CO-O-(3,5-(CH₃)₂-4-SCH₃-C₆H₂) | $n_D^{20}$: 1.5719 |
| 26 | C₆H₅-SO₂-N(C₃H₇)-S-N(CH₃)-CO-O-(3-CH₃-4-N(CH₃)₂-C₆H₃) | $n_D^{20}$: 1.5565 |
| 27 | C₆H₅-SO₂-N(C₃H₇)-S-N(CH₃)-CO-O-(2-(O-CO-C₃H₇)-C₆H₄) | $n_D^{20}$: 1.5570 |
| 28 | C₆H₅-SO₂-N(C₃H₇)-S-N(CH₃)-CO-O-(1-naphthyl) | viscous oil |
| 29 | 4-Cl-C₆H₄-SO₂-N(C₄H₉)-S-N(CH₃)-CO-O-N=C(1,3-dithiolan-2-ylidene) | viscous oil |
| 30 | 4-Cl-C₆H₄-SO₂-N(C₄H₉)-S-N(CH₃)-CO-O-N=C(CN)-C(CH₃)₃ | $n_D^{20}$: 1.5293 |
| 31 | 4-Cl-C₆H₄-SO₂-N(C₄H₉)-S-N(CH₃)-CO-O-N=C(SCH₃)(COOC₂H₅) | $n_D^{20}$: 1.5592 |
| 32 | 4-Cl-C₆H₄-SO₂-N(C₄H₉)-S-N(CH₃)-CO-O-N=C(SCH₃)(C(O)N(CH₃)₂) | $n_D^{20}$: 1.5528 |

TABLE 10—continued

| Compound No. | Formula | Physical properties |
|---|---|---|
| 33 | C₆H₅—SO₂—N(C₃H₇)—S—N(CH₃)—CO—O—[2-(2,2-dimethyl-1,3-dioxolan-yl)phenyl] | $n_D^{20}$: 1.5538 |
| 34 | (CH₃)₂N—SO₂—N(C₃H₇)—S—N(CH₃)—CO—O—N=C(CH₃)(SCH₃) | melting point 82° C. |
| 35 | (CH₃)₂N—SO₂—N(C₄H₉)—S—N(CH₃)—CO—O—N=C(CH₃)(SCH₃) | $n_D^{20}$: 1.5148 |
| 36 | (CH₃)₂N—SO₂—N(C₃H₇)—S—N(CH₃)—CO—O—(2,2-dimethyl-2,3-dihydrobenzofuran-7-yl) | $n_D^{20}$: 1.5331 |
| 37 | (CH₃)₂N—SO₂—N(C₄H₉)—S—N(CH₃)—CO—O—(2,2-dimethyl-2,3-dihydrobenzofuran-7-yl) | $n_D^{20}$: 1.5128 |
| 38 | (CH₃)₂N—SO₂—N(C₆H₅)—S—N(CH₃)—CO—O—(2,2-dimethyl-2,3-dihydrobenzofuran-7-yl) | melting point 114° C. |
| 39 | (CH₃)₂N—SO₂—N(C₆H₅)—S—N(CH₃)—CO—O—[3,5-dimethyl-4-(methylthio)phenyl] | melting point 147° C. |
| 40 | (CH₃)₂N—SO₂—N(C₆H₅)—S—N(CH₃)—CO—O—[3-methyl-4-(dimethylamino)phenyl] | melting point 116° C. |
| 41 | (CH₃)₂N—SO₂—N(C₆H₅)—S—N(CH₃)—CO—O—(2-isopropylphenyl) | $n_D^{20}$: 1.5505 |

TABLE 10—continued

| Compound No. | Formula | Physical properties |
|---|---|---|
| 42 | (CH₃)₂N-SO₂-N(phenyl)-S-N(CH₃)-CO-O-(2-(4,5-dimethyl-1,3-dioxolan-2-yl)phenyl) | $n_D^{20}$ : 1.5478 |
| 43 | (CH₃)₂N-SO₂-N(phenyl)-S-N(CH₃)-CO-O-(2-isopropoxyphenyl) | melting point 114° C. |

Other compounds which can be similarly prepared include the following

TABLE 11

(44) O₂N—C₆H₄—SO₂—N(C₃H₇)—S—N(CH₃)—CO—O—C₆H₄—CH₂—CH=CH₂

(45) (n-C₄H₉)(CH₃)N—SO₂—N(C₃H₇)—S—N(CH₃)—CO—O—C₆H₄—O—CH₂—C≡CH, with C₃H₇-n substituent

(46) C₆H₅—SO₂—N(C₆H₅)—S—N(CH₃)—CO—O—(6-(propylthio)naphthalen-2-yl)

(47) C₆H₅—SO₂—N(C₂H₅)—S—N(CH₃)—CO—O—N=C(2-phenyl-1,3-oxathiolane)

(48) (CH₃)₂N—SO₂—N(C₆H₅)—S—N(CH₃)—CO—O—N=C(5-methyl-1,3-dioxan)

C₆H₅—SO₂—N(C₂H₅)—S—N(CH₃)—CO—O—N=C(C(CH₃)₃)(P(OCH₃)₂=O)

---

It will be appreciated that the instant specification and examples are set forth by way of illustration and not limitation, and that various modifications and changes may be made without departing from the spirit and scope of the present invention.

What is claimed is:

1. An N-methyl-N-(sulphonic acid amide-N′-sulphenyl)-carbamic acid ester of the formula $$R^1-SO_2-N(R^2)-S-N(CH_3)-CO-O-R^3$$

in which $R^1$ is dialkylamino with 1 to 4 carbon atoms in each alkyl radical, phenyl or phenyl carrying at least one halogen, alkyl with 1 to 4 carbon atoms, nitro or trihalogenomethyl substituent, R² is alkyl with 2 to 8 carbon atoms, cycloalkyl, phenyl or cycloalkyl or phenyl carrying at least one halogen, alkyl with 1 to 4 carbon atoms, nitro or trifluoromethyl substituent, and R³ is phenyl, naphthyl, benzodioxolanyl, dihydrobenzofuranyl or indanyl; phenyl, naphthyl, benzodioxolanyl, dihydrobenzofuranyl or indanyl substituted at least once by trihalogenomethyl, halogen, nitro, cyano, cycloalkyl, formamidino, dioxanyl or dioxolanyl, or by alkyl with up to 4 carbon atoms, alkenyl with up to 4 carbon atoms, alkynyl with up to 4 carbon atoms, alkoxy with up to 4 carbon atoms, alkenoxy with up to 4 carbon atoms, alkynoxy with up to 4 carbon atoms, alkylmercapto with up to 4 carbon atoms, alkenylmercapto with up to 4 carbon atoms, alkynylmercapto with up to 4 carbon atoms, or dialkylamino with up to 4 carbon atoms per alkyl moiety.

2. A compound according to claim 1, in which R¹ represents dimethylamino or phenyl which can optionally be substituted by chlorine, methyl or trifluoromethyl, R² represents alkyl with 2 to 6 carbon atoms, cyclohexyl or phenyl, and R³ represents phenyl, which can optionally be substituted by alkyl with 1 to 3 carbon atoms, alkoxy with 1 to 3 carbon atoms, methylmercapto, dioxolanyl or methyl-substituted dioxolanyl, or represents benzodioxolanyl or dihydrobenzofuranyl which can optionally be substituted by methyl, or represents naphthyl.

3. An ester according to claim 1 wherein such ester is

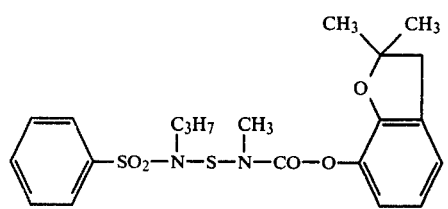

4. An ester according to claim 1 wherein such ester is

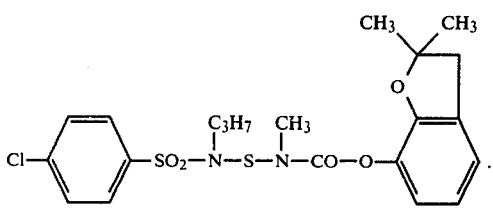

5. An ester according to claim 1 wherein such ester is

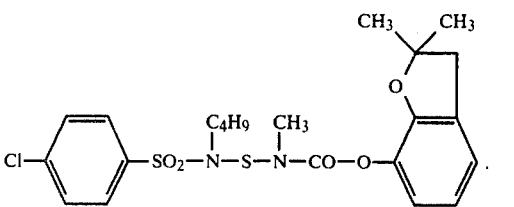

6. An ester according to claim 1 wherein such ester is

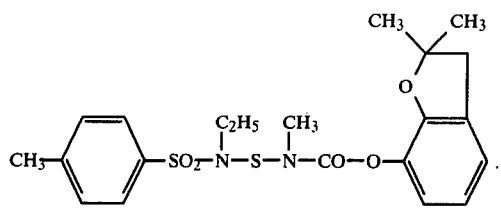

7. An ester according to claim 1 wherein such ester is

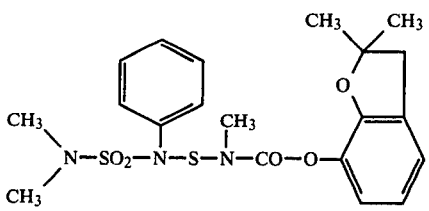

8. A nematicidal or arthropodicidal composition containing as active ingredient a nematicidally or arthropodically effective amount of an ester according to claim 1 in admixture with a diluent.

9. A method of combating nematodes or arthropods, which comprises applying to the nematodes or arthropods, or to a habitat thereof, a nematicidally or arthropodically effective amount of an ester according to claim 1.

10. The method according to claim 9 in which said ester is

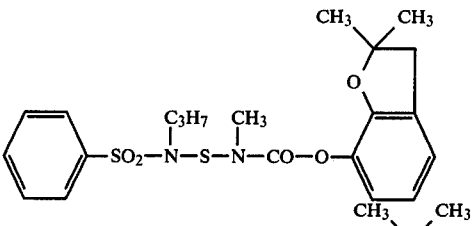

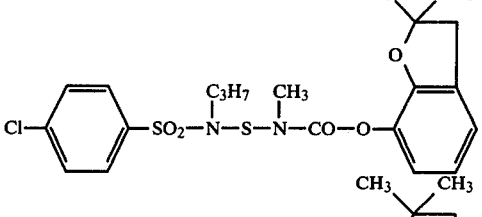

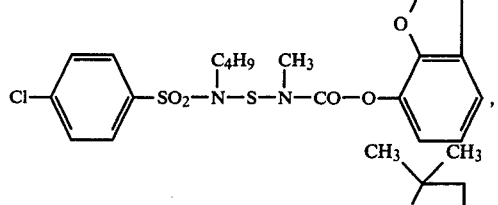

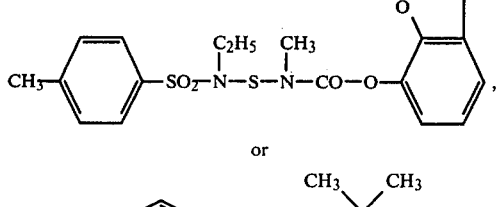

or

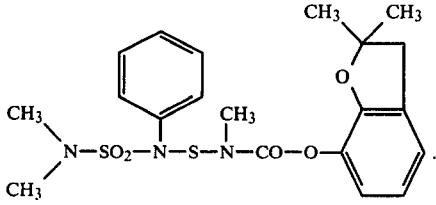

* * * * *